US006573078B1

(12) United States Patent
Wild et al.

(10) Patent No.: US 6,573,078 B1
(45) Date of Patent: *Jun. 3, 2003

(54) COMPOUNDS WHICH INHIBIT HIV REPLICATION

(75) Inventors: Carl T. Wild, Durham, NC (US); Thomas J. Matthews, Durham, NC (US); Dani P. Bolognesi, Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/464,003

(22) Filed: Jun. 2, 1995

Related U.S. Application Data

(63) Continuation of application No. 08/374,666, filed on Jan. 27, 1995, now Pat. No. 5,656,480, which is a continuation-in-part of application No. 07/927,532, filed on Aug. 7, 1992, now abandoned, which is a continuation-in-part of application No. 07/916,540, filed on Jul. 20, 1992, now abandoned.

(51) Int. Cl.[7] .......................... C12N 5/08; A61K 38/16
(52) U.S. Cl. ............................. 435/235.1; 424/188.1; 424/208.1; 530/324; 530/806; 514/12
(58) Field of Search ..................... 435/235.1; 514/12; 530/324, 806; 424/188.1, 208.1

(56) References Cited

U.S. PATENT DOCUMENTS

| | | | | | |
|---|---|---|---|---|---|
| 4,638,047 A | * | 1/1987 | Szelke et al. | ............... | 530/332 |
| 5,030,449 A | * | 7/1991 | Berzofsky et al. | ............ | 424/88 |
| 5,444,044 A | | 8/1995 | Jiang et al. | | |
| 5,656,480 A | * | 8/1997 | Wild et al. | ................... | 435/325 |

FOREIGN PATENT DOCUMENTS

| | | |
|---|---|---|
| EP | 0 323 157 | 7/1989 |
| EP | 0323157 | * 7/1989 |
| EP | 0 371 817 | 6/1990 |
| WO | WO 87/06005 | 10/1987 |
| WO | WO 94/16109 | 7/1994 |

OTHER PUBLICATIONS

B. J. Spalding, *Bio/Technology 10*, 24–29 (1992).
Nasar J. Qureshi et al. *AIDS*, 4, 553–558 (1990).
O'Shea et al. Science vol. 243 (1/89) 538–542.*
Wild et al., "PNAS, USA" 89, pp 10537–10541 (11/92).*
Crowl et al., "Cell" 41, pp 979–986 (1985).*
Leff, Bio Word Today, 1994 vol. 5 No. 210 pp.—1 & 5.*
Hammer et al, J. of Acq. Immunol Def. Syn., (1994) 7 (Suppl): 524–537.*
Saag et al., J. of Acq. Immunol Def. Syn., (1994) 7 (Suppl.):52–511.*
Davey et al., Proc. Natl. Acad. Sci, vol. 90, (1993) pp. 5608–5612.*
Richman et al, J. of Virology, (1994) vol. 68, No. 3, pp. 1660–1666.*
Crowl et al. HTLV–III env Gene Products Synthesized in *E Coli* are Recognized by Antibodies Present in the Sera of Aids Patients Cell 41(3) 979–86 Jul. 1985.*
Gallaher et al. Aids Research and Human Retrovirus, 5(4) (1969) 431–440.*
Detwart et al. AIDS Research and Human Retroviruses 6, 6 (1990) 703–706.*
Buckland et al. J Gen. Virol. 73(7) 1992 1703–1707.*
ASM News Jul. 1990 vol. 56(7) 368.*
Hammer, S.M. et al., 1994, "Issues in Combination Antiretroviral Therapy: A Review", J. Acq. Imm. Def. Syn. 7(Suppl. 2):S24–S37.
Richman, D.D. et al., 1994, "Nevirapine Resistance Mutations of Human Immunodeficiency Virus Type 1 Selected During Therapy", J. Virol. 68:1660–1666.
Saag, M.S. et al., 1994, "Pathogenicity and Diversity of HIV and Implications for Clinical Management: A Review", J. Acq. Imm. Def. Syn. 7(Suppl. 2):S2–S11.
Davey, R.T. et al., 1993, "Plasma Viremia as a Sensitive Indicator of the Antiretroviral Activity of L–697,661", Proc. Natl. Acad. Sci. (USA) 90:5608–5612.
Buckland, R. et al., 1992, "A Leucine Zipper Structure Present in the Measles Virus Fusion Protein is not Required for its Tetramerization but is Essential for Fusion", J. Gen. Virol. 73:1703–1707.
Dubay J.W. et al., 1992, "Mutations in the Leucine Zipper of the Human Immunodeficiency Virus Type 1 Transmembrane Glycoprotein Affect Fusion and Infectivity", J. Virol. 66:4748–4756.
Neurath, A.R. et al., 1992, "Synthetic Peptides and Anti–Peptide Antibodies as Probes to Study Interdomain Interactions Involved in Virus Assembly: the Envelope of the Human Immunodeficiency Virus (HIV–1)", Virology 188:1–13.
Spalding, B.J., 1992, "In Hot Pursuit of an HIV Vaccine", Bio/Technology 10:24–29.
Dubay, J.W. et al., 1991, "Structure–Function Analysis of the HIV Glycoprotein", Adv. Exp. Med. Biol. 303;39–46.
ASM News 56:368 (1990).

(List continued on next page.)

*Primary Examiner*—Bennett Celsa
(74) *Attorney, Agent, or Firm*—Pennie & Edmonds LLP

(57) ABSTRACT

This invention relates to human immunodeficiency virus (HIV) protein fragments which have antiviral activity, and particularly relates to HIV peptides derived from the HIV transmembrane glycoprotein (gp41) which inhibit HIV-induced cell-cell fusion. This invention further relates to methods for the inhibition of enveloped viral infection, and to methods that modulate biochemical processes which involve coiled coil peptide interactions.

26 Claims, 6 Drawing Sheets

OTHER PUBLICATIONS

Delwart, E.L. and Mosialos, G., 1990, "Retroviral Envelope Glycoproteins Contain a Leucine Zipper–Like Repeat", AIDS Res. and Human Retroviruses 6:703–706.

Qureshi, N.M. et al., 1990, "Characterization of a Putative Cellular Receptor for HIV–1 Transmembrane Glycoprotein Using Synthetic Peptides", AIDS 4:553–558.

Gallaher, W.R. et al., 1989, "A General Model for the Transmembrane Proteins of HIV and Other Retroviruses", AIDS Res. and Human Retroviruses 5:431–440.

Crowl, R. et al., 1985, "HTLV–III env Gene Products Synthesized in *E. coli* are Recognized by Antibodies Present in the Sera of AIDS Patients", Cell 41:979–986.

* cited by examiner

```
         558*
DP-107    NNLLRAIEAQQHLLQLTVWGIKQLQARILAVERYLKDQ
DP-121    NNLLRAIEAQQHLLQLTVWGPKQLQARILAVERYLKDQ
DP-125  CGGNNLLRAIEAQQHLLQLTVWGIKQLQARILAVERYLKDQ
                                                        609*
DP-31                                ERYLKDQQLLGIWGCSGKLICG
DP-116                          LQARILAVERYLKDQQQ
```

FIG. 1

COMPOUNDS WHICH INHIBIT HIV REPLICATION

This is a continuation of application Ser. No. 08/374,666, filed Jan. 27, 1995 now U.S. Pat. No. 5,656,480, which is a continuation-in-part of Ser. No. 07/927,532 filed Aug. 7, 1992 (abandoned) which is a continuation-in-part of Ser. No. 07/916,540 filed Jul. 20, 1992 (abandoned).

The present invention was made with Government support under grants numbers R01-AI30411 and P30-AI28662 from the National Institute of Allergy & Infectious Diseases. The Government has certain rights to this invention.

INTRODUCTION

This invention relates to human immunodeficiency virus (HIV) protein fragments which have antiviral activity, and particularly relates to HIV peptides derived from the HIV transmembrane glycoprotein (gp41) which inhibit HIV-induced cell-cell fusion. This invention further relates to methods for the inhibition of enveloped viral infection, and to methods that modulate biochemical processes which involve coiled coil peptide interactions.

BACKGROUND OF THE INVENTION

Numerous HIV protein fragments, or peptides, have been identified in an effort to develop an effective HIV vaccine. See generally B. Spalding, *Biotechnology* 10, 24 (Jan. 1992). Examples of patent applications which are directed to antigenic epitopes of the gp41protein include J. Rosen et al., PCT Application WO 87/06005 and R. Duncan, EPO Application 0 371 817. To date, the development of an anti-HIV vaccine has been difficult.

N. Qureshi et al., Aids 1990 4, 553–558, describe a segment of the HIV transmembrane protein (designated "gp41") which inhibits T-cell activation in vitro. This segment, designated "CS3", when conjugated to human serum albumin and labeled with fluorescein, binds specifically to CD4+ cell lines, and is said to have antiviral activity. CS3 comprises amino acids 581 to 597 of the gp41protein.

B. Kemp et al., EPO Application 0 323 157, describes a fragment comprised of amino acids 572 to 591 of the gp41protein which is said to have antiviral activity.

SUMMARY OF THE INVENTION

A first aspect of the present invention is a peptide selected from the group consisting of: (a) the peptide DP-107, which has the formula, from amino terminus to carboxy terminus, of:

NNLLRAIEAQQHLLQLTVWGIKQLQA-RILAVERYLKDQ (SEQ ID NO: 1); and (b) peptides of from 14 to 60 amino acids in length which form a heterodimer with the peptide DP-107 (SEQ ID NO: 1) (hereinafter on occasion referred to as "active compounds").

A second aspect of the present invention is a process for inhibiting HIV-induced cell fusion. The process comprises contacting to an HIV-infected cell an effective fusion-inhibiting amount of a peptide selected from the group consisting of: (a) the peptide DP-107, which has the formula, from amino terminus to carboxy terminus, of:

NNLLRAIEAQQHLLQLTVWGIKQLQA-RILAVERYLKDQ (SEQ ID NO: 1); and (b) peptides of from about 14 to 60 amino acids in length which form a heterodimer with the peptide DP-107 (SEQ ID NO: 1).

A third aspect of the present invention is a process for testing compounds for the ability to inhibit the ability of HIV to infect cells. The process comprises (a) contacting a test compound to a multimer of a peptide selected from the group consisting of: (i) the peptide DP-107, which has the formula, from amino terminus to carboxy terminus of:

NNLLRAIEAQQHLLQLTVWGIKQLQA-RILAVERYLKDQ (SEQ ID NO: 1) ; and (ii) peptides of from 14 to 60 amino acids in length which form a heterodimer with the peptide DP-107 (SEQ ID NO: 1); and then (b) detecting whether the test compound disrupts said multimer, the ability of the test compound to disrupt the multimer indicating the test compound is capable of inhibiting HIV infection of cells.

A further aspect of the invention is a method for inhibiting enveloped viral infection comprising contacting an uninfected cell with an effective amount of a peptide capable of contributing to the formation of a coiled coil peptide structure so that an enveloped virus is inhibited from infecting the uninfected cell.

The foregoing and other objects and aspects of the present invention are explained in detail in the drawings herein and the specification set forth below.

BRIEF DESCRIPTION OF THE DRAWINGS

FIG. 1 shows the sequences of various peptides studied. In DP-107 (SEQ ID NO: 1), DP-121 (SEQ ID NO: 2), and DP-125 (SEQ ID NO: 3) the leucine or isoleucine heptad repeat units are underlined. DP-107, DP-121, and DP-125 are acetylated at the $NH_2$ terminus and amidated at the COOH terminus. DP-116 (SEQ ID NO:4) (identical to the CS3 peptide) is amidated at the carboxy terminus and has a free amine terminus. DP-31 (SEQ ID NO: 5) is neither acetylated nor amidated. Amino acid residues are numbered according to Human Retroviruses and AIDS (1991).

DETAILED DESCRIPTION OF THE INVENTION

The term "HIV" as used herein refers to HIV-1, and the numbering of amino acids in HIV proteins and fragments thereof given herein is with respect to the HIV1$_{LAI}$ isolate. It is to be understood, however, that while HIV viral infection and the effects of DP-107 on such HIV infection are being used herein as a model systems in which -the potential anti-viral properties of peptides capable of forming coiled coils are described, such properties of coiled coil peptides may represent generalized mechanisms by which a broad spectrum of enveloped viral infections may be inhibited. Enveloped viruses whose infectivity may be inhibited using the coiled coil peptides of the invention may include, but are not limited to, other HIV strains such as HIV-2, as well as influenza viruses, syncytial respiratory viruses, an herpes viruses.

The DP107 peptide sequence is based on a highly conserved region in the transmembrane protein (TM) which was predicted by Gallaher et al., *AIDS Res. and Human Retro.* 5, 431 (1989), to form an extended amphipathic α-helix with structural analogues in the TM proteins of several fusogenic viruses such as influenza and other retroviruses. The function of the site is not known but may be related to multimerization of the envelope glycoprotein. The site has been shown to contain a "leucine zipper" repeat. See E. Delwart et al., *AIDS Res. and Human Retro.* 6, 703 (1990). The use of peptides such as DP-107 capable of forming coiled coils, therefore, may serve to interfere, block, or in some way modulate many biochemical processes which involve such coiled coil peptide formations. Such biochemical process may include, but are not limited to transcription factors (Abel and Maniatis, Nature 341:24) and physiological processes involving membrane fusion (White, J. M., 1992, Science 258:1917–1924).

Figure 4:
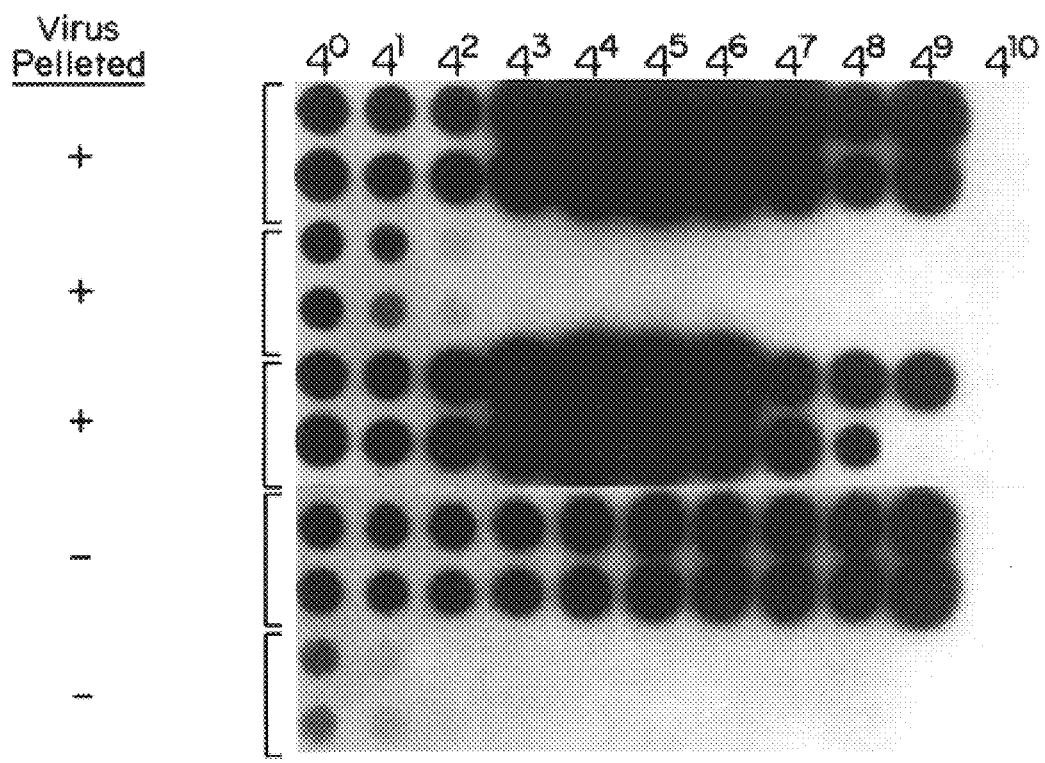
FIG. 4 shows the test for direct virocidal effect of peptides and soluble CD4 (sT4) The HIV-$1_{LAI}$ virus stock was divided into two portions. Samples of one portion (shown in figure as virus pelleted +) were treated for 2 hr at 37° C. in medium alone, with DP-107 at 40 mg/ml, or with sT4 at 10 mg/ml. Virus was then pelleted through a 5% sucrose layer to separate virus from non-associated inhibitor. The virus-containing pellets were dispersed in media and serial dilutions tested for infectivity on the AA5 cells. Serial four fold dilutions of the other portion of virus (virus pelleted –) were tested directly for infection of the cells with each dilution of virus incubated in the absence or presence of DP-107 at 40 mg/ml.

The biological activity of the eptide DP-107 was unexpected and its mechanism is not readily apparent. The results shown herein suggest that it does not act directly on the cell-free virions. Qureshi et al. (*AIDS* 4, 553 (1990)) have reported that an overlapping peptide, CS3 (DP-116 herein), inhibited infection when coupled to albumin and suggested that this occurred by attachment to a second receptor on the cell surface required for membrane fusion. These investigators have tentatively identified a candidate for the receptor as a 44 kD protein. Although such a mechanism would be consistent with the DP-107 result shown in FIG. 4 described hereinbelow, other observations argue that these two peptides are quite dissimilar and as such might function through peptide was only active after conjugation to albumin which contrasts with the striking anti-viral effect of the free (non-conjugated) DP-107 peptide. Also, the CS3 peptide showed no evidence for stable secondary structure by CD even at low temperatures and high concentrations, our experiments indicate that structure or capacity to assume stable secondary structure is a requirement for biological activity. For example, the DP-107 analogue containing a helix breaking proline substitution (DP-121) and several truncated versions of DP-107 (not shown) that either disrupted or failed to show stable solution structure did not exhibit anti-viral activity.

As noted above, a first aspect of the present invention is a peptide selected from the group consisting of:
  (a) the peptide DP-107, which has the formula, from amino terminus to carboxy terminus, of:
    N N L L R A I E A Q Q H L L Q L T V W G I K Q L Q A-RILAVERYLKDQ (SEQ ID NO:1); and
  (b) peptides of from 14 to 60 amino acids in length which form a heterodimer with the peptide DP-107 (SEQ ID NO: I)

In general, the peptide may be of any suitable length, but is preferably from 14 to 60 amino acids.in length, and more preferably from 16 to 38 amino acids in length. In addition, it will be appreciated that minor variations can be made to the peptide. For example, the peptide may be acetylated at the amino terminus thereof and/or amidated at the carboxy terminus thereof.

Peptides of the invention may be provided as multimers, particularly as dimers and tetramers. When provided in such form the multimer may be stabilized by covalently joining the monomers to one another. For example, a cysteine residue may be added to either (or both) ends of the monomer and monomers of the multimer covalently joined to one another by a disulfide bond between cysteine residues. Reactions are carried out in accordance with known techniques. In this manner two monomers of a dimer may be covalently joined to form a covalently stabilized dimer, and if desired two such covalently stabilized dimers conjugated to one another to form a tetramer. In another example, all four members of a tetramer could be covalently joined to one another through disulfide linkages between terminally positioned cysteine residues.

Other techniques for stabilizing the multimeric forms of these peptides include crosslinking the monomer components to one another through the formation of intermolecular amide bonds. This process involves the reaction of the amine moiety of a basic amino acid residue i.e. lysine, with the carboxy moiety of an acidic amino acid residue i.e. aspartic or glutamic acid.

Several techniques can used to determine the multimerization state of a given peptide or peptide mixture (homodimer or heterodimer). The most straightforward methods involve determining the apparent molecular weight of the multimer complex and from this determining the number of associated monomer components (this can be accomplished by dividing this apparent molecular weight by the molecular weight of the monomer). Analytical ultracentrifugation is a particularly suitable technique for this purpose. The specifics of this method are known to those skilled in the art. See., e.g., P. Graceffa et al., *J. Biol. Chem.* 263, 14196–14202 (1988), and can be summarized as follows. The material of interest is placed in a sample cell and spun very rapidly in a model E ultracentrifuge equipped with the appropriate detection devices. Information collected during the experiment combined with the amino acid composition of the peptide allows for the determination of the apparent MW of the multimer complex. Fast Protein Liquid Chromatography (FPLC) can also be used for this purpose. This technique is different from the above in that, as a type of chromatography, it ultimately requires reference back to some primary standard (determined by analytical ultracentrifugation). Pharmica Biosystems supplies the SUPERDEX 75™ column, which allows for the separation of the various multimeric forms of self-associating peptides. These determinations are carried out under non-denaturing (native) conditions and when referenced to the appropriate standards can be used to identify peptide and protein oligomerization states.

As will also be apparent to those skilled in the art, the test for heterodimerization may be carried out using either of the above two methods or through the use of CD combined with one or the other of these methods. This latter technique, in brief, involves adding known amounts of peptide to a solution containing a known amount of either the same peptide (for homodimerization) or a different peptide (for heterodimerization) and following the CD signal as a function of this addition. An increase in the magnitude of the signal as peptide is added indicates that the added material is participating in multimer formation. Homo vs heterodimerization is determined by carrying out this same experiment using FPLC or ultracentrifugation, which would determine if the resulting system is either single (hetero) or multi (homo) component. A second, and particularly preferred, approach to this same end is to conduct a CD melt on this same sample. If heterodimerization has occurred, then a single transition corresponding to the $T_m$ of the heterodimer will be observed (this $T_m$ value will probably be different from the value for either of the mixture components). If only homodimerization takes place then two transitions (two $T_m$'s) will be observed.

A process for inhibiting HIV-induced cell fusion, as also disclosed herein, comprising contacting to an HIV-infected cell an effective fusion-inhibiting amount of a peptide as given above. The process may be carried out in vitro in an aqueous solution, or may be carried out in vivo in a cellular culture assay for HIV infection (e.g., the CEM-SS cell monolayer plaque assay described in L. Kucera et al., *Aids Research and Human Retroviruses* 6, 491 (1990) or in an animal subject afflicted with the HIV virus- The process may be carried out with peptides of the invention in the form of multimers (particularly dimers) thereof as discussed above. The process may be carried out in a human or animal subject to prevent HIV-induced cell fusion, in which case the compounds may be combined with a suitable pharmaceutically acceptable carrier (such as sterile, pyrogen-free physiological saline solution, or sterile, pyrogen free phosphate-buffered saline solution), and administered to the subject by a suitable route (i.e., by intramuscular injection, subcutaneous injection, or intravenous injection). The therapeutic dosage is about 1 to 10,000 μg/Kg of patient weight per day, more particularly from about 10 to 1,000 μg/Kg of patient weight per day, and most particularly about 100 μg/Kg of patient weight per day. Thus, the present invention provides a method of combatting HIV (and particularly HIV-induced cell fusion) in a human or animal subject by administering an active compound as given herein in an effective HIV (or more particularly HIV-induced cell fusion)-combatting amount. The present invention also provides the use of an active compound as given herein for the preparation of a medicament for combatting HIV (or more particularly HIV-induced cell fusion) in a human or animal subject in need of such treatment.

A still further aspect of the present invention is a process, useful in rational drug design, for testing compounds for the ability to inhibit the ability of HIV to infect cells. The process comprises (a) contacting a test compound to a Multimer (e.g., dimer, tetramer) of a peptide as given above, and then (b) detecting whether the test compound disrupts said multimer, the ability of said test compound to disrupt said multimer indicating the test compound is capable of inhibiting HIV infection of cells. This process is noteworthy for its ability to identify compounds directed to a site which has not heretofore been explored in rational drug design. The process may be conveniently carried out in vitro in an aqueous solution containing the multimer by adding the test compound to the aqueous solution, and then determining whether or not the multimer structure has been disrupted. Disruption of multimer structure may be determined in the same manner as set forth above.

Note that amino acid sequences disclosed herein are presented in the amino to carboxy direction, from left to right. The amino and carboxy groups are not presented in the sequence. Amino acids are represented herein by one letter code or three letter code as follows:

| | |
|---|---|
| Ala; | A = Alanine |
| Arg; | R = Arginine |
| Asn; | N = Asparagine |
| Asp; | D = Aspartic acid |
| Cys; | C = Cysteine |
| Gln; | Q = Glutamine |
| Glu; | E = Glutamic Acid |
| Gly; | G = Glycine |
| His; | H = Histidine |
| Ile; | I = Isoleucine |
| Leu; | L = Leucine |
| Lys; | K = Lysine |
| Met; | M = Methionine |
| Phe; | F = Phenylalanine |
| Pro; | P = Proline |
| Ser; | S = Serine |
| Thr; | T = Threonine |
| Trp; | W = Tryptophan |
| Tyr; | Y = Tyrosine |
| Val; | V = Valine |

The foregoing abbreviations are in accordance with established usage. See, e.g., U.S. Pat. No. 4,871,670 to Hudson et al. at Col. 3 lines 20–43 (applicants specifically intend that the disclosure of this and all other patent references cited herein be incorporated herein by reference).

The present invention is explained in greater detail in the following Examples. These Examples are for illustrative purposes only, and are not to be taken as limiting of the invention.

EXAMPLE

Peptide Synthesis

Peptides DP-107 (SEQ ID NO: 1), DP121 (SEQ ID NO: 2), DP-125 (SEQ ID NO: 3), DP-116 (SEQ ID NO: 4), and DP-31 (SEQ ID NO: 5) were synthesized using FAST MOC™ chemistry on an Applied Biosystems Model 431A peptide synthesizer. Amidated peptides were prepared using Rink resin (Advanced Chemtech) while peptides containing free carboxy termini were synthesized on Wang (p-alkoxy-benzyl-alcohol) resins (Bachem). First residues were double coupled to the appropriate resin and subsequent residues were single coupled. Each coupling step was followed by acetic anhydride capping. Peptides were cleaved from the resin by treatment with TFA (10 ml), $H_2O$ (0.5 ml), thio-anisole (0.5 ml), ethanedithiol (0.25 ml), and crystalline phenol (0.75 g). Purification was carried out by reverse phase HPLC. Approximately 50 mg samples of crude peptide were chromatographed on a Waters DELTA PAK™ C18 column (19 mm×30 cm, 15 m spherical) using a linear gradient: $H_2O$/acetonitrile 0.1% TFA. Lyophilized peptides were stored desiccated and peptide solutions were made in water at about 5 mg/ml. Peptides stored in solution were stable for an extended period of time at 4° C. and could be repeatedly frozen and thawed with little apparent effect on biological activity.

The amino acid sequences of the peptides synthesized are shown in FIG. 1. DP-107 is a 38 amino acid peptide corresponding to residues 558 to 595 of the HIV-1 TM protein. Gallaher et al. (AIDS Res. and Human Retro. 5, 431 (1989)) and Delwart et al. (AIDS Res. and Human Reix-o. 6, 703 (1990)) observed that the primary sequence of this region was strongly predictive of a helical secondary structure and also contained a "leucine zipper" repeat. The amino terminus of the peptide was acetylated and the carboxy terminus amidated to reduce unnatural charge effects at those positions. DP-107 and each of the other peptides used in this study were purified by reverse phase HPLC and in each case the purified peptides gave a single symmetrical peak by analytical HPLC. The identity of each peptide was confirmed by electro-spray mass spectrometry, which yielded the following results: DP-107: 4526.71 (calculated 4526.31); DP-121: 4510.75 (calculated 4510.27) ; DP-116: 2057.32 (calculated 2056.44); DP-125: 4743.46 (calculated 4743.55); DP-31: 2479.35 (calculated 2480.93).

EXAMPLE

Evidence for Secondary Structure in Solution

Circular dichroism spectra were measured in 10 mM sodium phosphate, 150 mM sodium chloride, pH 7.0 buffer at approximately 10 mM concentrations using a 1 cm pathlength cell on a Jobin/Yvon Autodichrograph Mark V CD spectrometer. Peptide concentrations were determined from $A_{280}$ using Edlehoch's method (Biochemistry 6, 1948 (1967)).

Figure 2A:
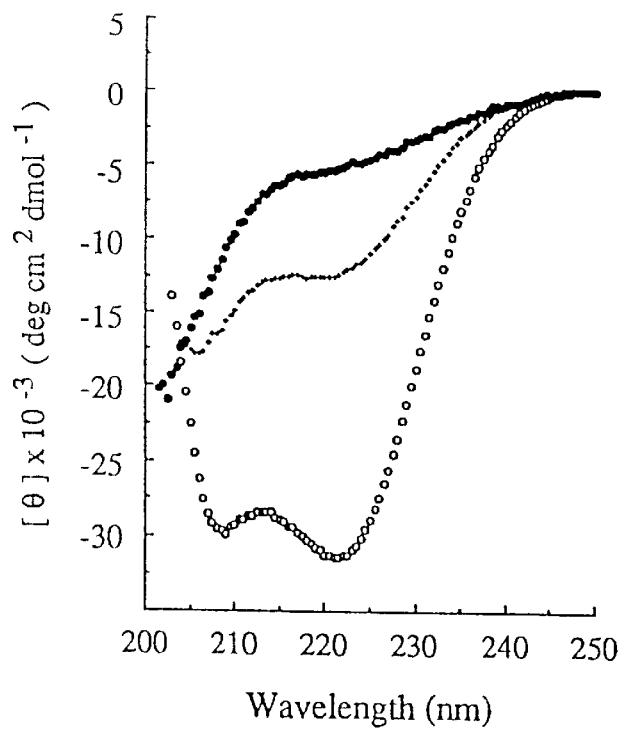
FIG. 2 shows the CD spectra of 10 mM solutions of DP-107(m), DP-121(+), and DP-116(1) at 0° C. (A) and 37° C. (B). Concentration dependence of the midpoint of the temperature dependence $(T_m)$ of the CD signal (C). $T_m$ corresponds to the maxima of the first derivative of the CD melt curve. The CD spectra were obtained in 10 mm sodium phosphate, 150 mM sodium chloride buffer at pH 7.0.
Figure 2B:
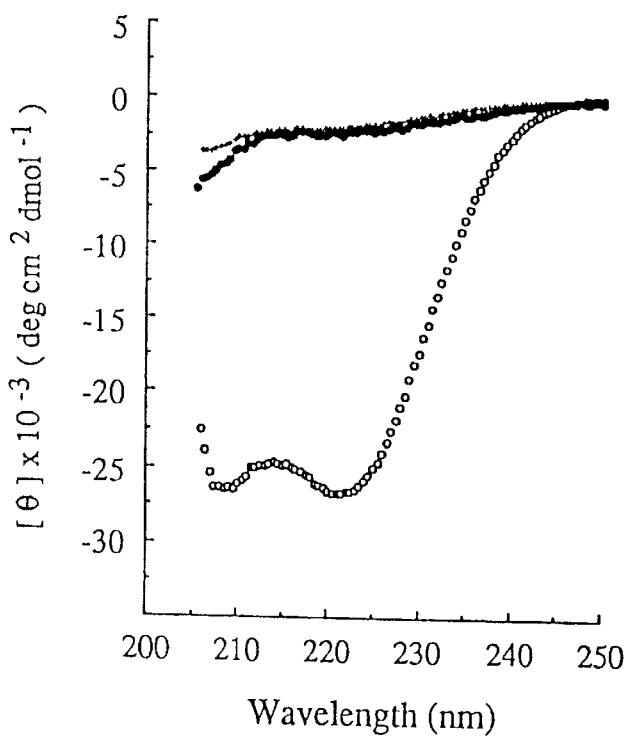
Figure 2C:
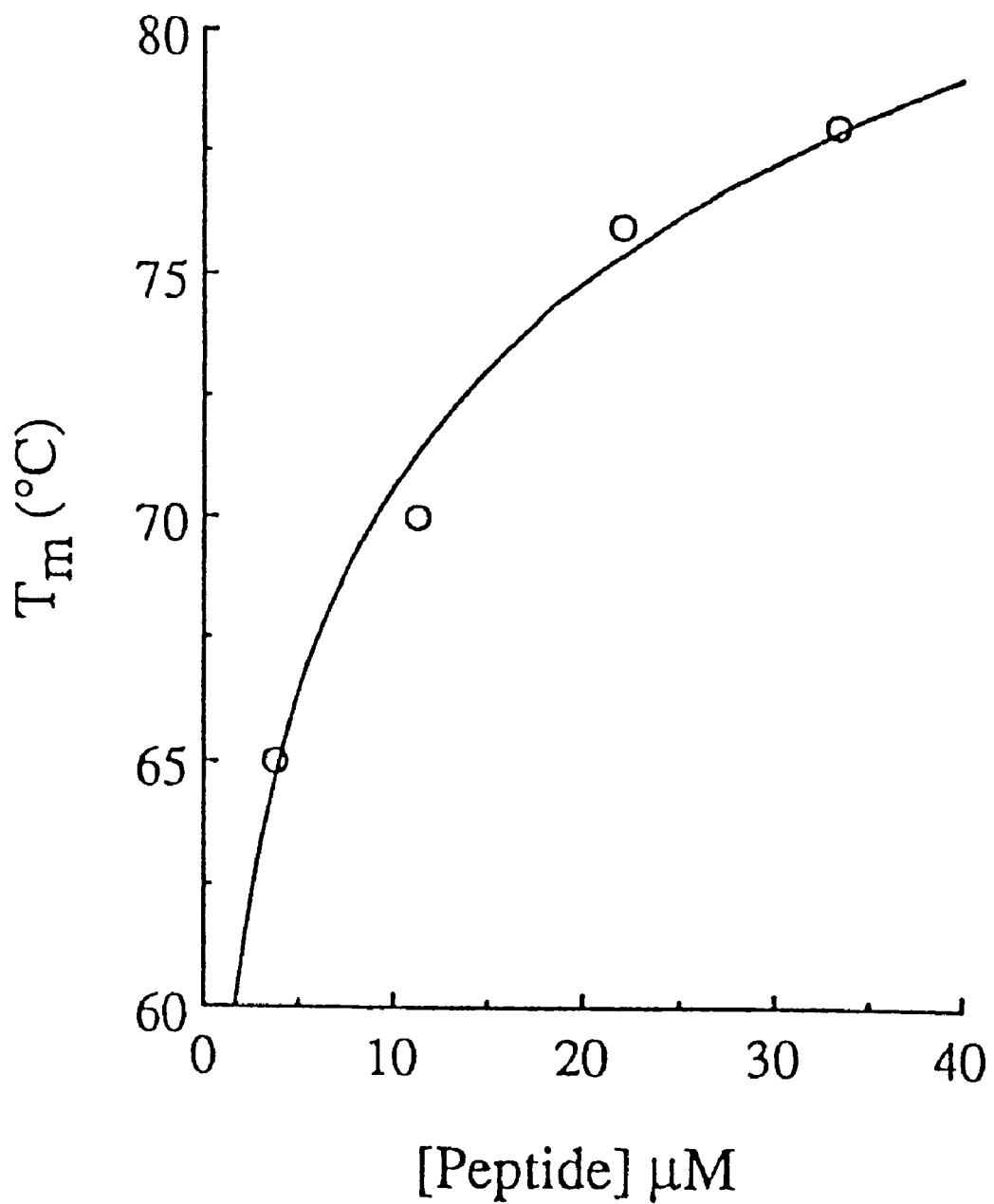

A summary of the ultraviolet CD analyses of DP-107 is shown in FIG. 2. The results suggest a considerable amount of secondary structure for the peptide under physiologic conditions. The double minima at 222 and 208 nm are characteristic of alpha helices and mean molar ellipticity values ($[Q]_{222}$) of −32,000 at 0° C. (FIG. 2A) and −27,000 at 37° C. (FIG. 2B) indicate that the peptide is approximately 100% and 85% folded at these temperatures (Y. Chen et al., Biochemistry 13, 3350 (1974); N. Greenfield & G. Fasman, Biochemistry 8, 4108 (1969)). The stability of the observed structure is illustrated by the thermal melt data shown in FIG. 2C. For example, at a 10 mM concentration of DP-107, the midpoint of the melting curve ($T_m$) was approximately 72° C. Also apparent in FIG. 2C is that the $T_m$ for DP-107 varies as a function of peptide concentration. This concentration dependence is characteristic of leucine zipper-type structures and is indicative of stabilization of secondary structural elements by self-association (E. O'Shea et al., Science 243, 538 (1989)). Oligomerization of DP-107 in solution to form dimers and tetramers is also suggested by sedimentation equilibrium studies. Taken together, the results shown in FIG. 2 tend to support the predictions (W. Gallaher et al., supra; E. Delwart et al., supra) that the region of gp41corresponding to DP-107 contains a leucine zipper-like (coiled coil) motif which may play a role in envelope oligomerization. This type of structure can be described as a homodimer formed by the specific (and often parallel) association of two alpha-helices. This interaction is characterized by the alignment of the hydrophobic faces of the helices. The unusually stable secondary structure exhibited by peptides involved in these types of systems is due to these higher- order interactions. Preliminary analysis of the solution structure of DP-107 by multi-dimensional nuclear magnetic resonance (NMR) spectroscopy indicates a large number of sequential NH—$NH_i$ crosspeaks in the NOESY spectra which is consistent with the CD evidence that under physiologic conditions, the peptide exhibits significant a-helical secondary structure.

The CD spectra of two other synthetic peptides are also shown in FIG. 2. One of these (DP-121) is identical to DP-107 but with the isoleucine at position 578 replaced with a proline residue. The other peptide, DP-116, is a 17 mer and overlaps the carboxy terminus of DP-107. This peptide was synthesized to contain the same amino acids and blocking groups as CS3, a peptide described by Qureshi et al. (AIDS 4, 553 (1990)) and reported to exhibit anti-viral activity when coupled to albumin. The CD spectra observed for these two peptides indicate that both exist in random coil conformations at 37° C. in direct contrast to the results obtained for DP-107. This outcome was expected for the proline substituted analogue, DP-121, in that the proline residue would tend to both break helix formation as well as disrupt hydrophobic interactions thought to stabilize coiled coil structures.

EXAMPLE

Reverse Transcriptase (RT) Assay

The micro RT assay was adapted from Goff et al. (J. Virol. 38, 239 (1981)) and Willey et al. (J. Virol. 62, 139 (1988)). Supernatants from virus/cell cultures are made 1% in Triton-X100. A 10 ml sample of supernatant was added to 50 ml of RT cocktail in a 96 well U bottom microtiter plate and the samples incubated at 370° C. for 90 min. The cocktail contained 75 mM KCl, 2 mM dithiothreitol, 5 mm Mgcl2l 5 mg/ml poly A (Pharmacia cat. No. 27-4110-01), 0.25 units/ml oligo dT (Pharmacia cat. No. 27-7858-01), 0.05% NP40, 50 mM Tris-HC1, pH 7.8, 0.5 mM non-radioactive dTTP, and 10 mCi/ml $^{32}$p-dTTP (Amersham cat. No. PB.10167). After the incubation period, 40 ml of reaction mixture was applied to a Schleicher and Schuell NA45 membrane (or DE81 paper) saturated in 2×SSC buffer (0.3M NaCl and 0.003M sodium citrate) held in a Schleicher and Schuell Minifold over one sheet of GB003 filter paper. Each well of the minifold was washed four times with 200 ml 2×SSC. The membrane was removed from the minifold and washed 2 more times in a pyrex dish with an excess of 2×SSC. Finally the membrane was drained on absorbent paper, placed on Whatman #3 paper, covered with saran wrap, and exposed to film overnight.

EXAMPLE

HIV-1 Virus Propagation

The $HIV1_{LAI}$ virus was obtained from R. Gallo (see M. Popovic et al., Science 224, 497 (1984)) and propagated in CEM cells cultured in RPMI 1640 containing 10-% FCS. Supernatant from the infected CEM cells was passed through a 0.2 mm filter and the infectious titer estimated in a microinfectivity assay using the AA5 cell line to support virus replication. For this purpose 25 ml of serially diluted virus was added to 75 ml AA5 cells at $2×10^5$/ml in a 96 well microtiter plate. Each virus dilution was tested in triplicate. Cells were cultured for eight days by addition of fresh medium every other day. On day 8 post infection supernatant samples were tested for virus replication as evidenced by RT activity released to the supernatant in accordance with the procedure described above. The $TCID_{50}$ was calculated according to the Reed and Muench formula in accordance with known techniques. See L. Reed et al., Amer. J. Hygiene 27, 493 (1938). The titer of the HIV-$1_{LAI}$ stock used for these studies, as measured on the AA5 cell line, was approximately $1\times10^7 TCID_{50}$/ml. The two primary isolates were obtained from PBMCs of two infected donors, one from Brazil (HIV-$1_{Br3}$) and the other Trinidad (HIV-$1_{Q72775}$) by co-cultivation with PHA-blasted normal donor PBMCs in RPMI 1640 containing IL2. The infectious titers of the primary virus stocks were estimated by titration onto normal human PHA blasted PBMCs in a 96 well microtiter plate, again using RT activity released to the supernatant as evidence for successful infection. The infectious titer of both of these isolates was estimated to be approximately $1\times10^3$ $TCID_{100}$/ml.

EXAMPLE

Peptide Inhibition of Infected Cell Induced syncytia Formation

The initial screen for antiviral activity of the peptides shown in FIG. 1 was for blockade of syncytium formation induced by overnight co-cultivation of uninfected Molt4 cells with chronically infected (HIV-$1_{IIIB}$) CEM cells.

Approximately $7\times10^4$ Molt cells were incubated with $1\times10^4$ CEM cells chronically infected with the HIV-$1_{LAI}$ virus in 96 well plates (one-half area cluster plates;Costar. Cambridge, Mass.) in a final volume of 100 ml culture media in accordance with known techniques (T. Matthews et al., Proc. Natl. Acad. Sci. U.S.A. 84, 5424 (1987)). Peptide inhibitors were added in a volume of 10 ml and the cell mixtures were incubated for 24 hr at 37° C. At that time point, multinucleated giant cells were estimated by microscopic examination at a 40× magnification which allowed visualization of the entire well in a single field.

The results of three such experiments are shown in Table 1. In the first of these, serial peptide concentrations between 50 $_K$g/ml and 1.5 mg/ml were tested for blockade of the cell fusion process. It is shown that DP-107 afforded complete protection down to a concentration of 6 mg/ml. The overlapping 17 mer peptide, DP-116, which is analogous to the previously described CS3 by Qureshi et al. (AIDS 4, 553 (1990)) exhibited no evidence of anti-fusogenic activity even at 50 mg/ml. This observation is in agreement with that study which only found anti-viral activity for CS3 after conjugation to albumin. A second peptide DP-31 representing an overlapping immunodominant site (M. Oldstone et al., J. Virol. 65, 1727 (1991); J. Wang et al., Proc. Natl. Acad. Sci. USA 83, 1659 (1986)) also failed to show inhibitory activity.

TABLE 1

Test for Peptide Blockade of HIV-1 Induced Cell—Cell Fusion

| Peptide | Syncytia Number Peptide Concentration (micrograms/ml) | | | | | | |
|---|---|---|---|---|---|---|---|
|  | 50 | 25 | 12 | 6 | 3 | 1.5 | 0 |
| EXP. 1 DP-31 | 85 | 80 | 78 | 87 | 90 | 75 | 89 |
| DP-116 | 89 | 82 | 93 | 92 | 89 | 82 | 89 |

TABLE 1-continued

Test for Peptide Blockade of HIV-1 Induced Cell—Cell Fusion

| Peptide | Syncytia Number Peptide Concentration (micrograms/ml) | | | | | | |
|---|---|---|---|---|---|---|---|
| DP-107 | 0 | 0 | 0 | 0 | 46 | 80 | 89 |
|  | 40 | 20 | 10 | 5 | 2.5 | 1.25 | 0 |
| EXP. 2 DP-107 | 0 | 0 | 0 | 36 | 83 | 98 | 93 |
| DP-125 | 0 | 0 | 0 | 0 | 3 | 35 | 93 |
| EXP. 3 DP-121 | 69 | 71 | 65 | 60 | 68 | ND | 76 |
| DP-125 | 0 | 0 | 0 | 0 | 0 | 0 | 76 |

The inhibitory activity of DP-107 did not appear related to cytotoxic or cytostatic effects since in other studies CEM cells grown in the presence of DP-107 at 50 mg/ml (the highest concentration tested) for three days with fresh peptide added each day displayed the same viability and growth rate as control cultures. We also found that DP-107 blocked fusion mediated by the other prototypic isolates: HIV-$1_{MN.RF.}$, and $_{SF2}$.

The concentration dependence of the CD spectra described suggests that the structure of the DP-107 is stabilized by peptide self association. In similar studies, O'Shea et al. (Science 243, 538 (1989)) reported that disulfide bridging of a peptide of the leucine zipper domain in the GCN4 protein (a transcriptional regulatory factor) to form covalently bonded homodimers stabilized the coiled coil structure. Following similar reasoning we sought to determine if the limiting effective concentration for cell fusion blockade by DP-107 might in part be related to the concentration dependence of peptide self-association. In order to test this possibility we synthesized a DP-107 analogue with a cysteine containing "tail" which after purification could be air oxidized to yield a homodimer. The resulting peptide, DP-125, exhibited about twice the apparent molecular weight of DP-107 in SDS-PAGE under non-reducing conditions indeed suggesting that a covalently bonded homodimer was generated. In the syncytial blocking assays (Table 1 experiments 2 and 3) this analogue was, in fact, more efficacious than DP107, requiring one-half to one-fourth the concentration for inhibition. The increased activity exhibited by as reproduced in all assays performed to date and suggests that a dimer or higher order multimer might actually represent the biologically active form of the peptide. Also, CD measurements of DP-125 were found to yield similar ellipticity values as the parental DP-107. Taken together these observations indicate that the individual peptide components of the putative multimers are arranged in a parallel rather than anti-parallel orientation.

To gain further insights as to whether the solution structure observed for DP-107 in the CD and NMR studies is required for biological activity, the proline-containing analog (DP-121))which failed to exhibit helix related signals a 37° C. in the CD experiments was tested for activity in the cell fusion assay. The results showed no sign of inhibitory activity as indicated in Table 1. Although this does not prove that structure is necessary for biological activity, it is consistent with that possibility. In a similar fashion, each of the DP-107 peptide analogues tested to date that failed to block cell fusion have also failed to show evidence of stable solution structure in CD studies. Also, a peptide which formed a coiled coil structure (GCN4-p1, provided by R. Rutkowski) exhibited no biological activity.

EXAMPLE

Peptide Inhibition of Infection by Cell-Free Virus

Figure 3:
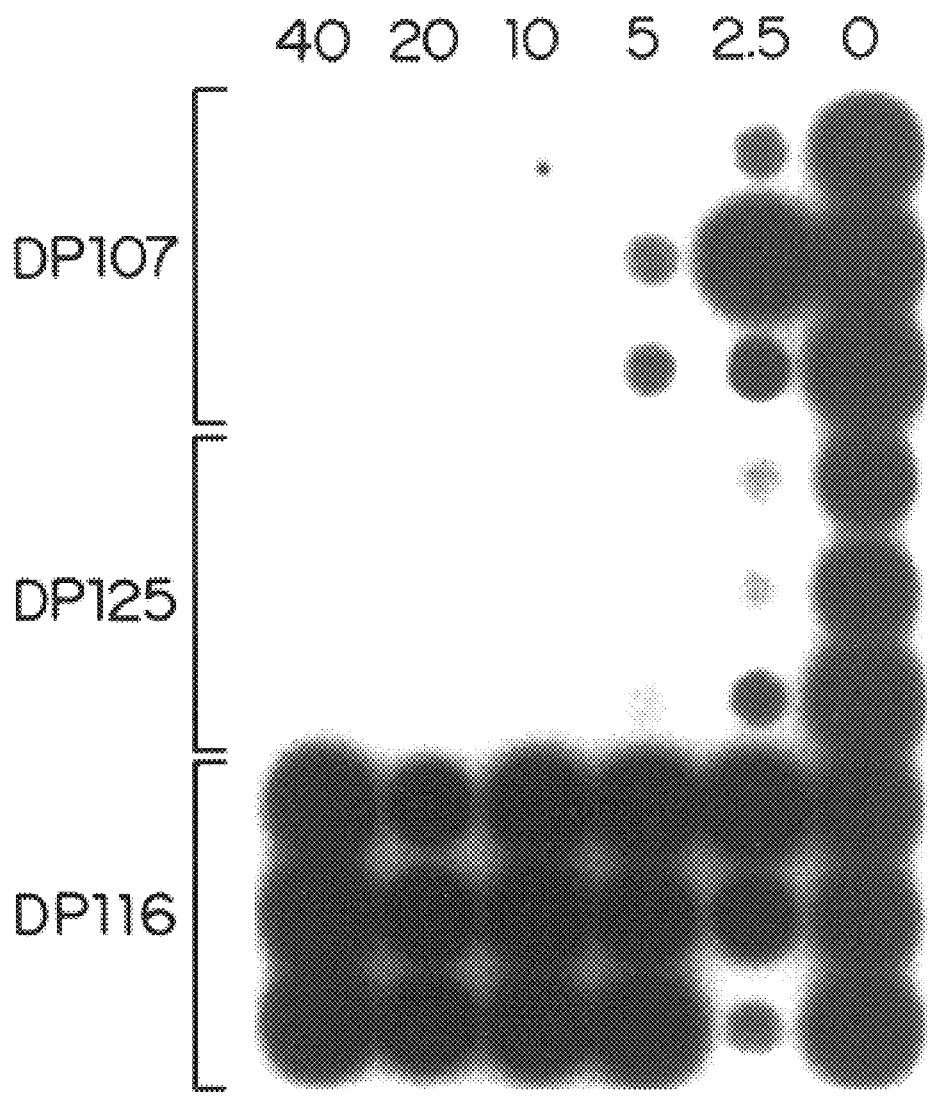
FIG. 3 shows the test for peptide blockade of AA5 cell infection by HIV-$1_{LAI}$ About 500 $TCID_{50}$ HIV-LAI were added to $2\times10^4$ AA5 cells and test peptides (final concentrations shown) in a final volume of 100 ml. Cell cultures were maintained in 96-well microtiter plates for 8 days by addition of fresh medium (but no further addition of peptides) every other day. On the eighth day post-infection, supernatant was tested for reverse transcriptase activity as evidence of successful infection.

The peptides were next tested for blockade of infection by cell-free virus. The results shown in FIG. 3 are representative of several experiments in which the DP-107, 125, and (CS3) peptides were compared for potency in the blockade of $HIV_{LAI}$, infection of AA5 cells. Each level of peptide was incubated in triplicate with about 500 $TCID_{50}$ of virus and cells. After 7 days of culture, cell-free supernatant was tested for the presence of RT activity as a measure of successful infection. The results are shown in FIG. 3 and demonstrate that both the DP-107 and DP-125 reagents inhibited the de-novo infection process at about the same effective doses as noted in the fusion assays described above. Moreover the dose required for inhibitory effect was lower for the disulfide bridged DP-125 analogue and no hint of anti-viral effect was noted for the DP-116 peptide.

EXAMPLE

Peptide Inhibition of PBMC Infection by Primary Isolates

Figure 5:
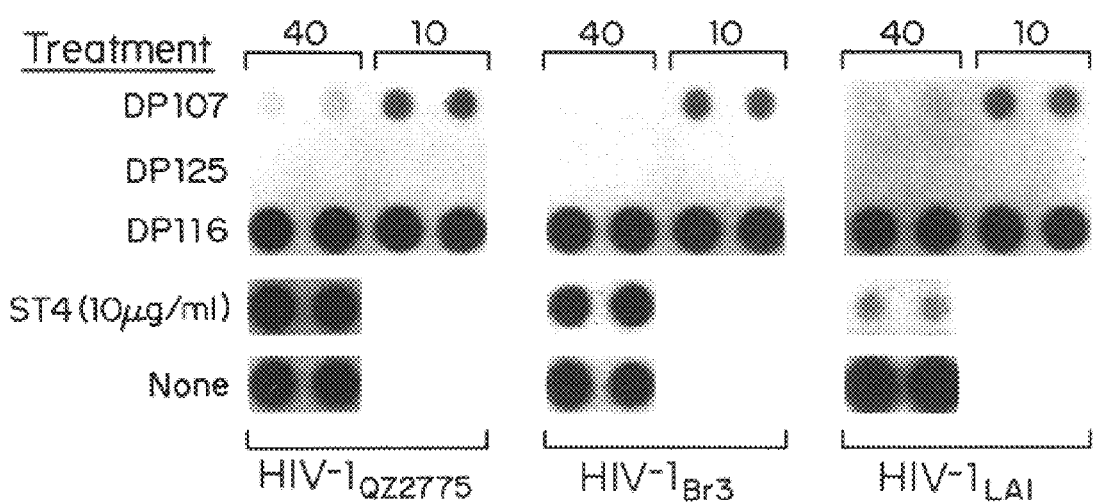
FIG. 5 shows a comparison of peptides and soluble CD4 to inhibit primary virus isolates. About 25 $TCID_{100}$ of two primary isolates and HIV-1$_{LAI}$ were added to PRA activated human PBMCs (about 1.5×10$^6$/ml) containing the indicated final concentrations of test peptide or 5T4. Each treatment condition was tested in duplicate and the cells were cultured in RPMI1640 containing 10% FCS 5% IL2. Four days post infection an equal number of fresh PBMCs were added to each well. This step allows for further expansion of virus and increases the noise to background ratio in the final RT assay. Supernatant was harvested 8 days after infection and tested for the presence of reverse transcriptase activity.

It is now apparent that substantial differences in sensitivity to anti-viral agents can exist between laboratory adapted prototypic isolates and primary field isolates passaged only through PBMCs. This problem was first highlighted by Ho and colleagues (E. Dear et al., Proc. Natl. Acad. Sci. 87, 6574 (1990)) in studies with soluble CD4. To test if the gp41 peptides might exhibit a similar discordance in reactivity, the DP-107, DP-125 (cysteine analogue), and sT4 (same reagent as used in the preceding experiment) were compared for inhibition of PBMC infection by two primary HIV-1 isolates and $HIV_{LAI}$. The results of these studies (FIG. 5) show that the peptides inhibit both the primary and prototypic isolates tested. Only a single dose of sT4 (10 mg/ml) was included for comparative purposes and it is apparent that this reagent is substantially more active on the cell-line adapted HIV-$1_{LAI}$ virus in comparison to the two primary isolates.

EXAMPLE

Synthesis of DP-107 Analogs

Analogs of DP-107 were synthesized in accordance with known techniques as given in Example 1 above. Such analogs are set forth in Table 2 below.

EXAMPLE

Activity of DP-107 Analogs

The activity of various DP-107 analogs as described herein was tested by the syncytia assay described in Example 5 above. These data are given in Table 3 below.

TABLE 3

| Peptide | [CONC] | No. Syncytia/well at peptide concentration, ug/ml on IIIB | | | | | |
|---|---|---|---|---|---|---|---|
| | | 40 | 20 | 10 | 5 | 2.5 | 1.25 | 0 |
| DP116 | 8.0 mg/ml | 77 | | | | | | |
| DP107 | 4.5 mg/ml | 0 | 0 | 0 | 4 | 68 | 88 | |
| DP118 | 3.9 mg/ml | 0 | 0 | 77 | 80 | 78 | 74 | |
| DP121 | 3.9 mg/ml | 79 | | | | | | |
| DP122 | 3.4 mg/ml | 73 | | | | | | |
| DP123 | 4.0 mg/ml | 4 | 55 | 86 | 76 | 69 | 80 | |
| DP125 | 3.1 mg/ml | 0 | 0 | 0 | 0 | 0 | 0 | |
| DP127 | 3.3 mg/ml | 0 | 0 | 0 | 20 | 53 | 87 | |
| DP129 | 3.4 mg/ml | 0 | 0 | 0 | 0 | 0 | 0 | |
| DP130 | 4.5 mg/ml | 0 | 0 | 0 | 0 | 0 | 47 | |
| Ctrl cells only | | | | | | | | 85 |

EXAMPLE

Biological Activity of DP-107 and Analogs Thereof

The biological activity of DP-107 and various analogs thereof in the fusion assay described in Example 5 above and the neutralization assay described in Example 6 above is summarized in Table 4 below. The quantity of compound required to produce a ninety percent reduction in number of syncytia is shown in the column marked "Fusion"; the quantity of compound required to produce a ninety percent reduction in infectivity is given in the column marked "Neutraliz". Compounds active in the fusion assay at a range between 20 and 40 4 μg/ml are considered moderately active; compounds active at a range between 10 and 20 μg/ml are considered potent; and compounds active in an amount of less than 10 μg/ml are considered very potent.

TABLE 2

DP-107 Analogs.

| | | |
|---|---|---|
| DP-118 | QQLLDVVKRQQEMLRLTVWGTKNLQARVTAIEKYLKDQ | (SEQ ID NO: 16) |
| DP-122 | GIKQLQARILAVERYLKDQQ | (SEQ ID NO: 6) |
| DP-123 | IEAQQHLLQLTVWGIKQLQARILAVERYLKDQ | (SEQ ID NO: 7) |
| DP-127 | NNLLRAIEAQQHLLQLTVWGIKQLQARILAV | (SEQ ID NO: 8) |
| DP-129 | NNLLRAIEAQQHLLQLTVWGIKQLQARILAVERYLKDQGGC | (SEQ ID NO: 9) |
| DP-130 | CGGNNLLRAIEAQQHLLQLTVWGIKQLQARILAVERYLKDQGGC | (SEQ ID NO: 10) |

TABLE 4

BIOLOGY OF DP-107 AND ANALOGS

| | | | Fusion [ug/ml]¹ | Neutraliz [ug/ml]² |
|---|---|---|---|---|
| DP-107 | (SEQ ID No: 1) | NNLLRAIEAQQHLLQLTVWGIKQLQARILAVERYLKDQ | 5 | 10 |
| DP-116 | (SEQ ID No: 4) | LQARILAVERYLKDQQQ | >40 | >30 |
| DP-121 | (SEQ ID No: 2) | NNLLRAIEAQQHLLQLTVWGPKQLQARILAVERYLKDQ | >40 | >30 |
| DP-122 | (SEQ ID No: 6) | GIKQLQARILAVERYLKDQQ | >40 | >30 |
| DP-123 | (SEQ ID No: 7) | IEAQQGLLQLTVWGIKQLQARILAVERYLKDQ | 40 | >30 |
| DP-125 | (SEQ ID No: 3) | CGNNLLRAIEAQQHLLQLTVWGIKQLQARILAVERYLKDQ | <1 | 2 |
| DP-127 | (SEQ ID No: 8) | NNLLRAIEQQHLLQLTVWGIKQLQARILAV | 7 | 23 |
| DP-129 | (SEQ ID No: 9) | NNLLRAIEAQQHLLQLTVWGIKQLQARILAVERYLKDQGGC | <1 | <1 |
| DP-130 | (SEQ ID No: 10) | CGGNNLLRAIEAQQHLLQLTVWGIKQLQARILAVERYLKDQGGC | 2 | <1 |
| DP-136 | (SEQ ID No: 11) | CGGNNLLRAIEAQQHLLQLTVWGIKQLQARILAV | >40 | >30 |
| DP-137 | (SEQ ID No: 12) | LSGIVQQQNNLLRAIEAQQHLLQLTVWGIKQLQARILAV | 12 | 12 |
| DP-138 | (SEQ ID No: 13) | CGGLSGIVQQQNNLLRAIEAQQHLLQLTVWGIKQLQARILAV | >40 | >30 |
| DP-139 | (SEQ ID No: 14) | NNLLRAIEAQQHLLQLTVWGSKQLQARILAVERYLKDQ | >40 | >30 |
| DP-140 | (SEQ ID No: 15) | NNLLRAIEAQQHLLQLTVWGAKQLQARILAVERYLKDQ | 17 | 14 |

¹90% reduction in number of syncytia (control = 90)
²90% reduction in infectivity
Bold letters = non-naturally occurring amino acid residues The foregoing examples are illustrative of the present invention, and are not to be construed as limiting thereof. The invention is defined by the following claims, with equivalents of the claims to be included therein.

---

What is claimed is:

1. An isolated peptide having the DP-107 amino acid sequence listed in SEQ ID NO:1.

2. The peptide of claim 1 wherein the amino terminus of the peptide is acetylated.

3. The peptide of claim 1 wherein the carboxy terminus of the peptide is amidated.

4. An isolated multimer of the peptide of claim 1.

5. The multimer of claim 4 wherein the multimer is a tetramer.

6. The multimer of claim 4 wherein the multimer is a dimer consisting of two peptide monomers.

7. The dimer of claim 6 wherein the monomers of the dimer are covalently bound to one another.

8. A method for inhibiting fusion of HIV to a cell comprising contacting the cell with a peptide in an effective amount to inhibit cell fusion, wherein the peptide is the peptide of claim 1.

9. The method of claim 8 wherein the HIV is HIV-1.

10. The method of claim 8 wherein the peptide is present as a multimer.

11. The method of claim 10 wherein the multimer is a dimer having two peptide monomers.

12. A method for inhibiting transmission of HIV to a cell comprising contacting the cell with a peptide in an effective amount to inhibit infection of the cell, wherein the peptide is the peptide of claim 1.

13. The method of claim 12 wherein the HIV is HIV-1.

14. The method of claim 12 wherein the peptide is present as a multimer.

15. The method of claim 14 wherein the multimer is a dimer having two peptide monomers.

16. The method of claim 15 wherein the monomers are covalently bound to one another.

17. An isolated peptide having the DP-125 amino acid sequence listed in SEQ ID NO:3.

18. An isolated peptide having the DP-127 amino acid sequence listed in SEQ ID NO:8.

19. An isolated peptide having the DP-129 amino acid sequence listed in SEQ ID NO:9.

20. An isolated peptide having the DP-130 amino acid sequence listed in SEQ ID NO:10.

21. An isolated peptide having the DP-137 amino acid sequence listed in SEQ D NO:12.

22. An isolated multimer of a peptide selected from the group consisting of DP-125 (SEQ ID NO:3), DP-127 (SEQ ID NO:8), DP-129 (SEQ ID NO:9), DP-130 (SEQ ID NO:10), and DP-137 (SEQ ID NO:12).

23. The multimer of claim 22, wherein the multimer comprises a dimer having two peptide monomers.

24. The multimer of claim 22, wherein the multimer comprises a tetramer.

25. A method for inhibiting fusion of HIV to a cell comprising contacting the cell with a peptide in an effective amount to inhibit cell fusion, wherein the peptide is selected from the group consisting of DP-125 (SEQ ID NO:3), DP-127 (SEQ ID NO:8), DP-129 (SEQ ID NO:9), DP-130 (SEQ ID NO:10), and DP-137 (SEQ ID NO:12).

26. A method for inhibiting transmission of HIV to a cell comprising contacting the cell with a peptide in an effective amount to inhibit infection of the cell, wherein the peptide is selected from the group consisting of DP-125 (SEQ ID NO:3), DP-127 (SEQ ID NO:8), DP-129 (SEQ ID NO:9), DP-130 (SEQ ID NO:10), and DP-137 (SEQ ID NO:12).

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 38 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
            35

(2) INFORMATION FOR SEQ ID NO:2:

(i) SEQUENCE CHARACTERISTICS:
      (A) LENGTH: 38 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:2:

Asn Asn Leu Leu Arg Ala Ile Glu Ala Gln Gln His Leu Leu Gln Leu
1               5                   10                  15

Thr Val Trp Gly Pro Lys Gln Leu Gln Ala Arg Ile Leu Ala Val Glu
            20                  25                  30

```
Arg Tyr Leu Lys Asp Gln
          35

(2) INFORMATION FOR SEQ ID NO:3:

(i) SEQUENCE CHARACTERISTICS:
        (A) LENGTH: 41 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:3:

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
            35                  40

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:4:

Leu Gln Ala Arg Ile Leu Ala Val Glu Arg Tyr Leu Lys Asp Gln Gln
1               5                   10                  15

Gln (2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:5:

Glu Arg Tyr Leu Lys Asp Gln Gln Leu Leu Gly Ile Trp Gly Cys Ser
1               5                   10                  15

Cys Lys Leu Ile Cys Gly
            20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:6:

Gly Ile Lys Gln Leu Gln Ala Arg Ile Leu Ala Val Glu Arg Tyr Leu
1               5                   10                  15
```

```
Lys Asp Gln Gln
         20

(2) INFORMATION FOR SEQ ID NO:7:

(i) SEQUENCE CHARACTERISTICS:
        (A) LENGTH: 32 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:7:

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr Leu Lys Asp Gln
            20                  25                  30

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val
            20                  25                  30

(2) INFORMATION FOR SEQ ID NO:9:

(i) SEQUENCE CHARACTERISTICS:
        (A) LENGTH: 41 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:9:

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln Gly Gly Cys
            35                  40

(2) INFORMATION FOR SEQ ID NO:10:

(i) SEQUENCE CHARACTERISTICS:
        (A) LENGTH: 44 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:10:

Cys Gly Gly Asn Asn Leu Leu Arg Ala Ile Glu Ala Gln Gln His Leu
1               5                   10                  15
```

```
Leu Gln Leu Thr Val Trp Gly Ile Lys Gln Leu Gln Ala Arg Ile Leu
            20                  25                  30

Ala Val Glu Arg Tyr Leu Lys Asp Gln Gly Gly Cys
        35                  40

(2) INFORMATION FOR SEQ ID NO:11:

(i) SEQUENCE CHARACTERISTICS:
         (A) LENGTH: 34 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:11:

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val (2) INFORMATION FOR SEQ ID NO:12:

(i) SEQUENCE CHARACTERISTICS:
         (A) LENGTH: 39 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:12:

Leu Ser Gly Ile Val Gln Gln Gln Asn Asn Leu Leu Arg Ala Ile Glu
1               5                   10                  15

Ala Gln Gln His Leu Leu Gln Leu Thr Val Trp Gly Ile Lys Gln Leu
            20                  25                  30

Gln Ala Arg Ile Leu Ala Val
        35

(2) INFORMATION FOR SEQ ID NO:13:

(i) SEQUENCE CHARACTERISTICS:
         (A) LENGTH: 42 amino acids
         (B) TYPE: amino acid
         (C) STRANDEDNESS:
         (D) TOPOLOGY: unknown (ii) MOLECULE TYPE: peptide (xi) SEQUENCE DESCRIPTION: SEQ ID NO:13:

Cys Gly Gly Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Val
        35                  40

(2) INFORMATION FOR SEQ ID NO:14:

(i) SEQUENCE CHARACTERISTICS:
         (A) LENGTH: 38 amino acids
         (B) TYPE: amino acid
         (C) STRANDEDNESS:
         (D) TOPOLOGY: unknown
```

-continued

```
    (ii) MOLECULE TYPE: peptide (xi) SEQUENCE DESCRIPTION: SEQ ID NO:14:

Asn Asn Leu Leu Arg Ala Ile Glu Ala Gln Gln His Leu Leu Gln Leu
1               5                   10                  15

Thr Val Trp Gly Ser Lys Gln Leu Gln Ala Arg Ile Leu Ala Val Glu
            20                  25                  30

Arg Tyr Leu Lys Asp Gln
        35

(2) INFORMATION FOR SEQ ID NO:15:

(i) SEQUENCE CHARACTERISTICS:
        (A) LENGTH: 38 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:15:

Asn Asn Leu Leu Arg Ala Ile Glu Ala Gln Gln His Leu Leu Gln Leu
1               5                   10                  15

Thr Val Trp Gly Ala Lys Gln Leu Gln Ala Arg Ile Leu Ala Val Glu
            20                  25                  30

Arg Tyr Leu Lys Asp Gln
        35

(2) INFORMATION FOR SEQ ID NO:16:

(i) SEQUENCE CHARACTERISTICS:
        (A) LENGTH: 38 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:16:

Gln Gln Leu Leu Asp Val Val Lys Arg Gln Gln Glu Met Leu Arg Leu
1               5                   10                  15

Thr Val Trp Gly Thr Lys Asn Leu Gln Ala Arg Val Thr Ala Ile Glu
            20                  25                  30

Lys Tyr Leu Lys Asp Gln
        35
```